United States Patent [19]

Gustafson et al.

[11] 4,170,645

[45] Oct. 9, 1979

[54] ANTIBACTERIAL AGENT BM123γ, SALTS AND ALKYL DERIVATIVES THEREOF FOR THE CONTROL OF SHIPPING FEVER IN CATTLE

[75] Inventors: Richard H. Gustafson, Lawrenceville; Gordon A. Kemp, Princeton, both of N.J.

[73] Assignee: American Cyanamid Company, Stamford, Conn.

[21] Appl. No.: 925,660

[22] Filed: Jul. 17, 1978

[51] Int. Cl.$^2$ ............... A61K 31/71; A61K 31/415; A61K 31/35
[52] U.S. Cl. ................... 424/181; 424/273 R; 424/283; 424/272
[58] Field of Search ............... 424/181, 272, 273, 283

[56] References Cited

U.S. PATENT DOCUMENTS

| | | | |
|---|---|---|---|
| 4,007,167 | 2/1977 | Martin et al. | 424/181 |
| 4,018,972 | 4/1977 | Hlavka | 424/181 |
| 4,048,431 | 9/1977 | Hlavka et al. | 424/181 |

*Primary Examiner*—Sam Rosen
*Attorney, Agent, or Firm*—H. G. Jackson

[57] ABSTRACT

The invention is novel methods for the control of shipping fever in cattle, comprising administering parenterally to the animals a pharmaceutically effective amount of the antibiotic BM123γ, pharmaceutically acceptable salts, and alkyl derivatives thereof. This invention further relates to the antibiotic BM123γ, pharmaceutically acceptable salts, and alkyl derivatives thereof, which have beneficial effect of controlling shipping fever in cattle.

7 Claims, No Drawings

ANTIBACTERIAL AGENT BM123γ, SALTS AND ALKYL DERIVATIVES THEREOF FOR THE CONTROL OF SHIPPING FEVER IN CATTLE

The beef cattle industry is engaged in large scale shipping of cattle on a regular basis. As a result of shipping, and other conditions which introduce stress in the animals, a febrile respiratory disease is often seen in young cattle, commonly referred to as shipping fever.

Shipping fever is caused by combinations of stress, a viral infection and a bacterial infection. The bacterial portion of the disease may be treated with effective antibacterial agents, resulting in rapid clinical improvement. This acute respiratory disease is characterized clinically by fever, depression, anorexia, nasal dischage, acute inflammation of the air-ways, pneumonia, necrosis of the tissues involved, and is a major cause of illness and death among young cattle.

Considering the relatively large frequency with which it is to be found among young cattle, this disease had adverse economic effects on feedlot operators and the entire beef industry. Thus, shipping fever manifesting itself among cattle in deaths, weight losses, inefficient feed conversion, delayed marketing, and expensive treatments, is directly responsible for enormous financial losses suffered by the beef cattle industry, and ultimately by the consumer.

It is, therefore, of considerable interest and of advantage to find suitable antibacterial agents and methods of use thereof for the control of shipping fever in beef cattle.

Surprisingly, we have discovered that shipping fever can be effectively controlled in beef cattle by parenterally administering to the host animal a pharmaceutically effective amount of antibiotic BM123γ, pharmaceutically acceptable salts, and alkyl derivatives thereof, represented by formula (I)

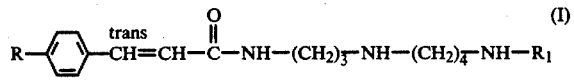

wherein $R_1$ is hydrogen, alkyl $C_1$-$C_{10}$, halo substituted alkyl $C_2$-$C_6$ or hydroxy substituted alkyl $C_2$-$C_6$; and wherein R is a moiety of:

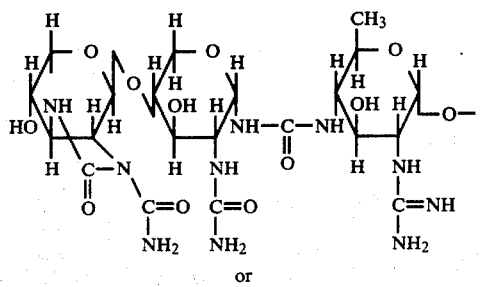

or

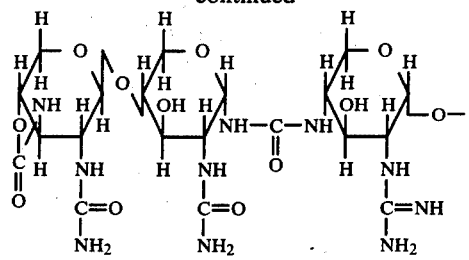

and mixtures thereof.

A preferred group of compounds represented by formula (I) above are those wherein $R_1$ is hydrogen, isopropyl, 1,3-dimethylbutyl, 1,3,3trimethylbutyl, 1,2-dimethylpentyl, 1-methylnonyl, 1-ethyl-3-chloropropyl or 1-methyl-2-hydroxypropyl.

Pharmaceutically acceptable acids, which may be used to prepare salts of said antibiotics are, among others, hydrochloric acid, sulfuric acid, phosphoric acid, citric acid, tartaric acid and the like.

The antibiotics BM123γ1 and γ2 are formed by fermentative biosynthesis during the cultivation under controlled conditions of an undetermined species of Nocardia, NRRL 5646 and, in particular, by a mutant strain of NRRL 5646, namely NRRL 8050 and more particularly by an X-ray mutant of NRRL 8050, namely Lederle KL 1192, a viable culture of which has been deposited with the Culture Collection Laboratory, Northern Utilization Research and Development Division, U.S. Department of Agriculture, Peoria, Ill. and has been added to its permanent collection under their accession number NRRL 11230 where it is freely available to the public.

The preparation and properties of antibiotics BM123γ1 and γ2, hereinafter referred to as BM123γ, pharmaceutically acceptable salts, and alkyl derivatives thereof, as well as the diagnostic characteristics of NRRL 5646 and NRRL 8050 are set forth in U.S. Pat. No. 4,007,167 (1977); U.S. Pat. No. 4,018,972, (1977), and in U.S. Pat. No. 4,048,431 (1977).

Lederle KL 1192 (NRRL 11230) has cultural, physiological and morphological characteristics essentially the same as those of NRRL 8050.

In accordance with this invention, shipping fever of cattle can be effectively controlled by administering a hereinabove identified compound of formula (I) to the host animal in an amount from about 0.25 to 2.0 mg/kg body weight and preferably 0.50 to 1.0 mg/kg body weight daily, in the form of one or more subcutaneous, intramuscular or intravenous injection(s) or as one or more subcutaneous implant(s), designed to release continuously over an extended period of time the formula (I) antibiotic in amounts sufficient to maintain an effective concentration of drug in the animals' circulatory system to control the bacterial pathogens of shipping fever.

In practice, the active material is formulated as injectables using pharmaceutically acceptable solvents, buffers, preservatives and other additives.

Injectables for subcutaneous, intramuscular or intravenous administration may be prepared by dissolving a pharmaceutically acceptable salt of a formula (I) antibiotic BM123γ at a concentration of from 1% to 20% and preferably 1% to 5% w/v in double distilled water, wherein the solution may also contain 0.6 to 0.8% w/v of a phosphate or citrate buffer, 0.4 to 0.6% w/v sodium chloride, preservatives such as methyl paraben, propyl paraben in amounts of 0.1% to 0.2% w/v, disodium Edetate and the like. If desired some of the water may be replaced in the formulations with water miscible and pharmaceutically acceptable solvents, such as propylene glycol, glycerol, glycerol formal, and the like.

Alternatively, a premeasured amount of freeze-dried antibiotic BM123γ of formula (I) may be prepackaged in multiples of unit dosages in sterile vials and reconstituted with predetermined volumes of sterile water, isotonic saline solution, mixtures of water - propylene glycol, - glycerol, - glycerol formal, and the like, prior to use.

Alternatively, the active material may be formulated as implants, which, in addition to the drug may contain pharmaceutically acceptable carriers, lubricants and other additives generally used in such formulations, wherein the composition of the implant is so designed as to release the active material into the circulatory system of the host animal over a period of time, at a rate sufficient to control the bacterial pathogens of shipping fever.

Whether the implant is in the form of a paste or a pellet is a matter of choice. Pellet-type implants which can be used in accordance with this invention may be prepared by admixing from about 50% to 95% by weight of a compound of the formula (I) antibiotic BM123γ compound with from about 50% to 5% by weight of a pharmaceutically acceptable carrier such as Castorwax (i.e., glyceryl 12-hydroxystearate), white wax, beeswax, starch, or a high molecular weight (i.e., 4000) polyethylene glycol, or mixtures thereof, alone or in combination with a small amount of a lubricant such as zinc stearate or magnesium stearate. A small polyvinylpyrrolidone of polyvinylpurrolidone and dibutylphthalate may also be incorporated in the above formulations.

Paste implants can be prepared using the same percentages of drug as stated above, but employing a mixture of high molecular weight (i.e., 4000) polyethylene glycol and low molecular weight (i.e., 400) polyethylene glycol alone, or in combination with, Castorwax or beeswax and/or polyvinylpyrrolidone.

Implants may vary in size and weight, but usually range between 10 mg. and 100 mg. per implant. Advantageously, with this method of application, the drug can be administered at periodic intervals throughout the treatment period of the animals. Moreover, formulations and intervals between implantations can be varied to provide a daily drug release of generally about 0.25 mg. to 2.0 mg. per kg. of body weight, and preferably 0.50 mg. to 1.0 mg. per kg. of body weight.

The following non limiting Examples serve to further illustrate the novel method of the invention.

EXAMPLE 1

In vivo activity of BM123γ-hydrochloride and of isopropyl BM123γ for the control of shipping fever in calves.

Two hundred sick calves, with elevated temperatures and clinical signs of shipping fever are chosen for the experiment. The animals are allotted to four groups of 50 calves each. One group serves as nonmedicated, infected controls receiving placebos, the other groups receive intramuscular injections of the respective drugs for three or four consecutive days at the levels indicated in Table 1. Those animals, whose initial temperatures were above 40.0° C. have reduced fevers, as shown in Table 1.

Freeze-dried samples of antibiotic BM123γ-hydrochloride and antibiotic isopropyl-BM123γ-hydrochloride are stored in sealed ampules, and are reconstituted with sterile distilled water prior to use, to a w/v concentration to yield injectables wherein a 2 ml dose per 45.36 kg (100 lbs) body weight contains the equivalent of one or the other drug at 2 mg/kg or 1 mg/kg body weight respectively.

TABLE I

Efficacy of test drugs in depressing the body temperature of calves having shipping fever.

| Group | Compound | Dosage mg/kg | Mean Initial Temperature | Temperature 2 days after last Injection | | |
|---|---|---|---|---|---|---|
| | | | | Mean in °C. | Calves below 39.4° C./total | Percent |
| 1 | Placebo | — | 40.6 | 39.7 | 14/36 | 39 |
| 2 | BM123γ . HCl | 2 | 40.5 | 39.3 | 25/37 | 68 |
| 3 | Isopropyl BM123γ | 1 | 40.5 | 39.2 | 26/37 | 70 |
| 4 | Oxytetracycline | 13 | 40.7 | 39.4 | 22/38 | 58 |

At the end of the experiment, six calves are sacrificed, and animal tissues examined for aerobic and anaerobic bacteria. Pasteurella are isolated and identified from three of the sacrificed calves. No anaerobes are recovered from any tissues. The results of bacterial isolations are summarized in Table II below.

a. The carcass was thin and dehydrated. There was a copious pink pleural effusion with cranio-ventral fibrous adhesions of both cardiac lobes. There was red hepatization of the right apical, right cardiac, left cardiac and 20-30% of the diaphragmatic lobes, as well as diffuse miliary abscessation of the lung. The liver was pale tan.

b. The carcass was emaciated and all tissues were pale. Lung lobes were consolidated with grey hepatization in 10% of their lobes and by red hepatization in 5%. There were a moderate number of miliary abscesses in the consolidated portions. The abomasum contained numerous helminths, probably haemonchus and trichostrongylus, and had edematous and slightly hyperemic mucosa. The duodenum contained helminths also. There was a moderate amount of serous effusion in the peritoneal cavity.

c. The carcass was emaciated and tissues were generally pale on initial incision. No lesions of pneumonia were found in the lungs. The abomasal mucosa was mildly hyperemic and edematous with numerous ostertagia nodules and haemonchus worms in the lumen. The gall bladder was edematous and the bile was slightly darkened.

d. The carcass was thin and dehydrated. The lungs were consolidated and had miliary abscesses in 60% of their volume. Bronchial and mediastinal lymph nodes were swollen, edematous and slightly hemorrhagic. The abomasal mucosa was hyperemic with numerous erosions. The kidneys contained mucoid material in the ducts and pelvis and hemorrhage in the calyces.

e. The calf was thin, dehydrated and ataxic prior to euthanasia. The lungs contained organized abscesses in right apical and right and left cardiac lung lobes. The abomasal mucosa was hemorrhagic and there was congestion in the large intestinal mucosa.

f. The calf was in good health and carcass condition other than an injury to the right hip. No visible lesions were seen except a 2×6 cm area of consolidation in the right apical lung lobe.

TABLE II

Pathogens isolated from the tissues of calves, treated with the antibacterial agents of the Invention.

| Calf. No. | | Compound | No of days administered | Bacteria isolated | Total *cfu/g |
|---|---|---|---|---|---|
| 1 | a | Placebo | 4 | P. hemolytica | $2.6 \times 10^7$ |
| 2 | b | Placebo | 4 | none | — |
| 3 | c | Placebo | 4 | none | — |
| 4 | d | oxytetracycline | 4 | P. Hemolytica + P. multocida | $9.1 \times 10^6$ |
| 5 | e | BM123γ . HCl | 4 | P. hemolytica | $4.5 \times 10^2$ |
| 6 | f | Isopropyl BM123γ | 1 | none | — |

*cfu = colony forming units

No bacteria are isolated from liver, spleen or kidney samples. Pasteurella is recovered almost exclusively from lung tissue. A low level of P. hemolytica ($<10^2$ cfu/g) is recovered from the mediastinal lymph node of Calf No. 1.

Minimal inhibitory concentrations (MIC) of eight Pasteurella isolates are also determined.

Isopropyl BM123γ and BM123γ-hydrochloride are similar in activity, and both are more active than oxytetracycline and gentamicin against P. hemolytica in vitro. The results obtained are shown in Table III below.

TABLE III

In vitro, minimal inhibitory concentrations of Isopropyl BM123γ and BM123γ-hydrochloride against Pasteurella.

| | | MIC (mcg/ml) | | | |
|---|---|---|---|---|---|
| No. | Isolate | BM123γ . HCl | Isopropyl BM123γ | Gentamicin | Oxytetracycline |
| 1 | P. hemolytica | .12 | .25 | 4 | >32 |
| 2 | P. hemolytica | .25 | .5 | 8 | >32 |
| 3 | P. hemolytica | .12 | .12 | 2 | 64 |
| 4 | P. hemolytica | <.06 | .12 | 4 | 32 |
| 5 | P. hemolytica | .25 | .25 | 4 | .5 |
| 6 | P. multocida | .5 | .5 | 2 | .25 |
| 7 | P. multocida | .5 | .5 | 2 | .25 |
| 8 | P. multocida | .25 | .25 | 2 | .25 |

EXAMPLE 2

In vivo activity of Isopropyl BM123γ for the control of shipping fever in young cattle as compared to oxytetracycline.

Calves weighing 90.6 to 181.2 Kg received at the feedlot are processed as is normally done, except no antibacterial treatment is given. Processing includes vaccination with Infectious Bovine Rhinotracheitis (Bovine virus Diarrhea) Leptospirosis vaccine, administration of a Clostridium novyi, septicum, sordelli, chauvei bacterin, levamisole (½ oblet), i.m. administration of 3 ml of a vitamin A, D and E formulation, a pour-on formulation of 0,0-dimethyl-0-(2,4,5-trichlorophenyl) ester of phosphorothioic acid for the control of grubs and lice, and one DES (diethylstilbestrol) implant in an ear. In addition—and at the same time—the calves are branded, ear tagged, dehorned and castrated where applicable.

One to two days after arrival and processing, sick calves are removed from the holding pens and those with temperatures of 40.0° C. or higher and showing symptoms of respiratory disease are selected for the study.

A total of 300 calves are randomly allotted to four groups of 75 calves each. One group serves as infected unmedicated controls receiving a "blank" solution, the others receive intramuscularly between hip and pin bones, for a total of 3 daily injections of:

a. 11 mg/kg body weight of oxytetracycline, the maximum recommended dose;

b. 0.5 mg/kg body weight of Isopropyl BM123γ; or c. 1.0 mg/kg body weight of Isopropyl BM123γ.

The preparation and composition of injectables for "b" and "c" are described in Example 5 below.

Temperatures are recorded daily until two successive readings of 39.7° C. or lower are recorded, at which time calves are moved from the "sick" pen to the "recovered" pen. Although some of the "recovered" calves continue to show symptoms of disease, the criterion of body temperature is selected since it is completely objective.

One hundred fifty-four calves are treated the first day, fifty the second and 96 the third day. Following treatment, each animal is observed and its temperature recorded for a total of 14 consecutive days. Each animal which dies is necropsied and duplicate samples of lung and mediastinal lymph node are taken for microbiological examination. Necropsy examinations confirm the presence of severe pneumonia in most animals which died.

Mortality information is presented in Table IV below. The data contained therein do not include two calves treated with 1.0 mg/kg body weight of Isopropyl BM123γ, and one treated with 0.5 mg/kg body weight of Isopropyl BM123γ, since the causes of death were due to coccidiosis, an abdominal abcess following castration or a throat abcess, probably due to improper use of a balling gun prior to shipment, respectively. These calves died early in the study from conditions which the treatments should not have been expected to control.

TABLE IV

Mortality, and average number of days to return to normal temperature.

| Compound | Dosage mg/kg | Mortality No. of Animals | Mortality Percent | Days to Normal No. of Animals | Days to Normal No. of Days |
|---|---|---|---|---|---|
| Control | — | 17 | 22.7 | 63 | 5.95 |
| Oxytetracycline | 11.0 | 4 | 5.6 | 72 | 5.33 |
| Isopropyl BM123γ | 0.5 | 5 | 6.7 | 71 | 3.59 |
| Isopropyl BM123γ | 1.0 | 5 | 6.7 | 71 | 3.88 |

Number of animals may total to more than 75 per group because of relapses and mortality following two normal temperature days.

EXAMPLE 3

In vitro determination of the potency of Isopropyl BM123γ compared with oxytetracycline and gentamicin in selected bacterial isolates by a tube dilution method.

Serial two-fold dilutions of antibacterial agent are prepared in trypticase soy broth. To each tube containing 5 ml of broth, is added 0.1 ml of $10^{-3}$ dilution of bacterial inoculum, adjusted prior to dilution of 44 percent transmission at 645 m,u. An inoculated broth, containing no drug is included as growth for each strain tested. The minimum inhibitory concentration (MIC) is read as the highest dilution of drug showing no visible growth after 24 hours incubation at 37° C. The results obtained are summarized in Table V.

TABLE V

Minimum inhibitory concentrations of Isopropyl BM123γ against selected bacterial isolates (in vitro).

| Infective Organism | Isolate No. | MIC (mcg/ml) Isopropyl BM123γ | MIC (mcg/ml) Gentamicin | MIC (mcg/ml) Oxytetracycline |
|---|---|---|---|---|
| P. multocida | 1 | 2.0 | 4.0 | 64.0 |
| | 2 | 2.0 | 4.0 | 64.0 |
| | 3 | 2.0 | 8.0 | 1.0 |
| | 4 | 2.0 | 4.0 | 64.0 |
| | 5 | 4.0 | 4.0 | >64.0 |
| | 6 | 0.5 | 4.0 | >64.0 |
| | 7 | 2.0 | 4.0 | 1.0 |
| P. hemolytica | 1 | 1.0 | 8.0 | 2.0 |
| | 2 | 1.0 | 8.0 | 2.0 |
| | 3 | 8.0 | 4.0 | >64.0 |
| | 4 | 0.5 | 8.0 | 64.0 |
| | 5 | 0.5 | 4.0 | 64.0 |

EXAMPLE 4

In vitro antibacterial activity of Isopropyl BM123γ.

Pathogens are obtained from diseased animals. Minimal inhibitory concentrations (MIC) are determined for Pasteurella of bovine lung and lymph node origin and *mycoplasma* of bovine origin. Standard tube dilution techniques are used for these assays except for *mycoplasma*. *Mycoplasma* from cattle are examined by the agar dilution method using Steer's multiple inocula replicator. The results are presented in Table IV below.

TABLE VI

Minimal inhibitory concentrations of Isopropyl BM123γ against bovine pathogens.

| Pathogens | No. of Isolates | MIC (in mcg/ml) Range | MIC (in mcg/ml) Median |
|---|---|---|---|
| Pasteurella spp. | 40 | 0.125–1.0 | 0.5 |

TABLE VI-continued

Minimal inhibitory concentrations of Isopropyl BM123γ against bovine pathogens.

| Pathogens | No. of Isolates | MIC (in mcg/ml) Range | MIC (in mcg/ml) Median |
|---|---|---|---|
| Mycoplasma spp. | 20 | <0.07–20.0 | 1.8* |

*Geometric mean.

It can be seen from the above Table that Isopropyl BM123γ is active against the pathogens tested.

Minimal bactericidal concentrations (MBC) and minimal inhibitory concentrations of Isopropyl BM123γ are determined for 15 randomly selected Pasteurella pathogens obtained from pneumonic cattle lungs. The results are presented in Table VII below, where it can be clearly seen that the median MBC of Isopropyl BM123γ is two times of the median MIC.

TABLE VII

Minimal bactericidal and minimal inhibitory concentrations of Isopropyl BM123γ, tested on 15 Pasteurella isolates.

| Pasteurella spp. | Isoproyl BM123γ MBC* | Isoproyl BM123γ MIC** |
|---|---|---|
| Range | 0.5–4.0 | 0.25–1.0 |
| Median | 1.0 | 0.5 |

*Highest tube dilution of drug yielding no visible growth when 0.01 ml is inoculated to trypticase-soy-agar containing 5% sheep blood.
*Standard tube dilution technique.

We claim:
1. A method for the control of shipping fever in cattle comprising administering parenterally to the animals a pharmaceutically effective amount of antibiotic BM123γ represented by formula:

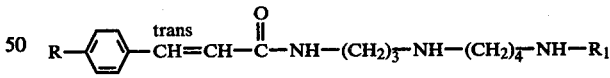

wherein $R_1$ is hydrogen, alkyl $C_1$–$C_{10}$, halo substituted alkyl $C_2$–$C_6$, or hydroxy substituted alkyl $C_2$–$C_6$; and wherein R represents a moiety of:

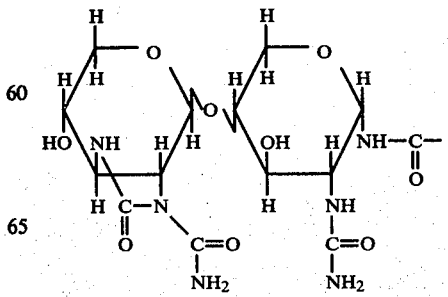

-continued

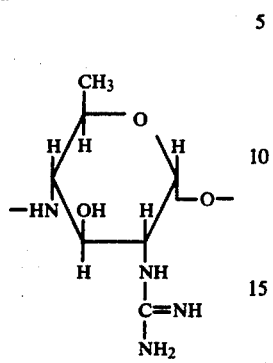

or

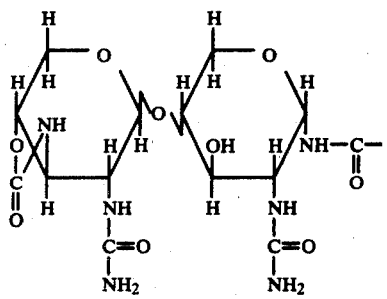

-continued

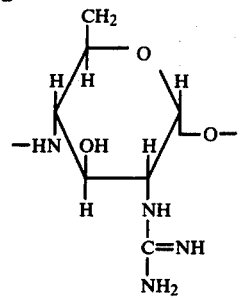

or mixtures thereof; or pharmaceutically acceptable salts thereof.

2. A method according to claim 1, wherein $R_1$ is hydrogen, isopropyl, 1,3-dimethylbutyl, 1,3,3-trimethylbutyl, 1,2-dimethylpentyl, 1-methylnonyl, 1-ethyl-3-chloropropyl and 1-methyl-2-hydroxypropyl; or pharmaceutically acceptable salts thereof.

3. A method according to claim 1, wherein the pharmaceutically acceptable salts are hydrochloride, sulfate, phosphate, citrate or tartrate.

4. A method according to claim 1, wherein the compound is administered in amounts from 0.25 mg/kg to 2.0 mg/kg body weight per day.

5. A method according to claim 1, wherein the antibiotic is BM123γ or isopropyl BM123γ.

6. A method according to claim 1, wherein antibiotic BM123γ hydrochloride is administered parenterally to cattle in amounts of from 0.25 mg/kg to 2.0 mg/kg body weight per day.

7. A method according to claim 1, wherein antibiotic isopropyl BM123γ is administered parenterally to cattle in amounts of from 0.25 mg/kg to 2.0 mg/kg body weight per day.

* * * * *